(12) United States Patent
Nelson et al.

(10) Patent No.: US 6,478,264 B1
(45) Date of Patent: Nov. 12, 2002

(54) PEEL TEST MANDREL ASSEMBLY AND METHOD

(75) Inventors: Lewis Nelson, Denison, TX (US); William P. Sammons, Denison, TX (US)

(73) Assignee: Sonoco Development, Inc., Hartsville, SC (US)

( * ) Notice: Subject to any disclaimer, the term of this patent is extended or adjusted under 35 U.S.C. 154(b) by 0 days.

(21) Appl. No.: 09/460,926

(22) Filed: Dec. 14, 1999

(51) Int. Cl.$^7$ .............................. F16L 3/00; G01N 19/04
(52) U.S. Cl. ..................... 248/65; 73/150 A; 73/827; 73/856; 138/106; 138/108
(58) Field of Search .................. 248/65; 73/150 A, 73/827, 856; 138/106–109, 140, 141, 145, 146, 148

(56) References Cited

U.S. PATENT DOCUMENTS

| | | | | |
|---|---|---|---|---|
| 753,399 A | * | 3/1904 | Hunt | 248/65 |
| 1,485,345 A | * | 2/1924 | Fleming | 248/654 X |
| 1,938,975 A | | 12/1933 | Parks | |

(List continued on next page.)

FOREIGN PATENT DOCUMENTS

| | | | | |
|---|---|---|---|---|
| CA | 1012947 | * | 6/1977 | 242/72 |
| DE | 853 832 | | 10/1952 | |
| DE | 30 21 482 A1 | | 12/1981 | G01L/5/00 |
| DE | 36 39 685 A1 | | 5/1988 | G01N/3/56 |
| GB | 551126 | | 2/1943 | 73/150 A |
| GB | 2130071 A | * | 5/1984 | 248/65 |
| GB | 2 196 437 | | 4/1988 | G01N/19/04 |
| JP | 3-272456 | | 4/1991 | G01N/29/00 |
| JP | 4-151543 | | 5/1992 | G01N/19/04 |
| JP | 6-201573 | | 7/1994 | G01N/19/04 |
| SU | 425075 | | 9/1974 | 73/150 A |
| SU | 715979 | | 2/1980 | 73/150 A |
| SU | 1067415 A | | 1/1984 | |
| SU | 1458773 A | | 2/1989 | G01N/19/04 |
| SU | 1716396 A1 | | 2/1992 | G01N/19/04 |
| SU | 1718051 A1 | | 3/1992 | G01N/19/04 |

OTHER PUBLICATIONS

Derwent–Acc–No: 1975–J7587W, Chekonov SU456131 A "Taper gauge for draw part mandrels—has adjustable stop in treasuvse direction to rod axis", Mar. 1975.*

(List continued on next page.)

Primary Examiner—Thomas P. Noland
(74) Attorney, Agent, or Firm—Drinker Biddle & Reath LLP

(57) ABSTRACT

A mandrel assembly is provided for testing the peel strength between an outer layer and an adjacent inner layer of a tubular laminate. The assembly includes a cylindrical mandrel rotatably mounted to a clamping bracket. The mandrel has a retaining surface on its outer periphery which frictionally retains a sleevedly mounted sample of the laminate. The mandrel is attached to an axle by a pair of rotational bearings. The axle is fixedly attached to the mounting bracket. The mounting bracket is generally L-shaped and has a radial leg radiating from the axle and a clamping leg for being clamped into a testing machine. Testing the peel strength of the laminate includes mounting a test sample onto the mandrel assembly, mounting the assembly in a conventional tensile testing machine, attaching a starting end of the outer layer of the sample to the testing machine, starting the machine and measuring the force required to peel the outer layer from the inner layer.

6 Claims, 2 Drawing Sheets

U.S. PATENT DOCUMENTS

| | | | | |
|---|---|---|---|---|
| 2,053,262 A | * | 9/1936 | Cornell, Jr. | 248/65 |
| 2,604,783 A | | 7/1952 | Herrlinger | 73/150 |
| 2,917,955 A | * | 12/1959 | Leger | 81/7.5 |
| 2,992,555 A | | 7/1961 | Butler | |
| 3,170,321 A | | 2/1965 | Sullivan et al. | |
| 3,312,460 A | * | 4/1967 | Kaufman | 73/827 X |
| 3,336,797 A | | 8/1967 | Raffalovich | 73/150 |
| 3,372,583 A | | 3/1968 | Van Beek | 73/150 |
| 3,380,289 A | | 4/1968 | Walters et al. | |
| 3,394,588 A | | 7/1968 | Mohle et al. | 73/150 |
| 3,412,606 A | | 11/1968 | Cooper et al. | 73/150 |
| 3,417,327 A | | 12/1968 | Breidenbach | 324/54 |
| 3,580,065 A | | 5/1971 | Strittmater et al. | 73/150 |
| 3,597,966 A | | 8/1971 | Heyman | |
| 3,683,682 A | | 8/1972 | Jochmann | 73/150 X |
| 3,788,135 A | | 1/1974 | Hammond, Jr. | 73/150 A |
| 3,793,879 A | | 2/1974 | Fowler | |
| 3,884,215 A | * | 5/1975 | Schlosser | 248/65 X |
| 4,065,964 A | | 1/1978 | Cunningham | 73/150 A |
| 4,194,392 A | | 3/1980 | Lombard et al. | 73/150 A |
| 4,432,246 A | | 2/1984 | Granat | 73/862.53 |
| 4,716,766 A | | 1/1988 | Baureis | 73/827 |
| 4,790,509 A | * | 12/1988 | Cardwell et al. | 248/65 X |
| 4,856,325 A | | 8/1989 | Tomita et al. | 73/150 A |
| 4,893,503 A | | 1/1990 | Kimura et al. | 73/150 A |
| 4,926,694 A | | 5/1990 | Crews, Jr. et al. | 73/794 |
| 4,942,769 A | | 7/1990 | Järvinen et al. | 73/821 |
| 5,085,074 A | | 2/1992 | Nolte et al. | 73/150 A |
| 5,103,678 A | | 4/1992 | Covino-Hrbacek et al. | 73/828 |
| 5,111,701 A | | 5/1992 | Klein | 73/827 |
| 5,168,752 A | | 12/1992 | Konermann et al. | 73/150 R |
| 5,176,028 A | * | 1/1993 | Humphrey | 73/150 A |
| 5,181,424 A | | 1/1993 | Martin et al. | 73/835 |
| 5,239,873 A | | 8/1993 | Cox | 73/845 |
| 5,267,710 A | * | 12/1993 | Condon | 248/65 |
| 5,404,751 A | | 4/1995 | Beran et al. | 73/150 A |
| 5,454,260 A | | 10/1995 | Wang | 73/150 A |
| 5,561,251 A | | 10/1996 | Greminger et al. | 73/865.8 |
| 5,596,133 A | | 1/1997 | Maciejewski | 73/7 |
| 5,629,487 A | | 5/1997 | Mücke et al. | 73/818 |
| 5,671,634 A | | 9/1997 | Donovan | 73/150 A |
| 5,944,060 A | * | 8/1999 | MacKay | 138/140 |
| 5,984,242 A | * | 11/1999 | Meyer | 248/65 |
| 6,098,932 A | * | 8/2000 | Olesen | 248/65 |
| 6,149,107 A | * | 11/2000 | Kerri et al. | 248/65 X |

OTHER PUBLICATIONS

Derwent–Acc–No: 1978—85553A, Lapslin SU 588135 A "Gluing elastic material to article—has article rotating against material laid on moving plate", Jan. 1978.*

Derwent–Acc–No: 1987–361252, Licrko et al SU 1310159 A "Bush press insertion machine—has additional pressing mandrels mounted on brakets on bush rotating round base mounted column, . . . ", May 1987.*

Derwent–Acc–No: 2000–301777 Arkhorov, RU 2130586 C1 "Device for measurement of deviation in distance between intersecting axes at outer and inner cylindrical surface", May 1999.*

NASA Tech brief 65–10173, "Peel Resistance of Adhesive Bonds Accurately Measured", Jun. 1965 1 page in 73/150A.

* cited by examiner

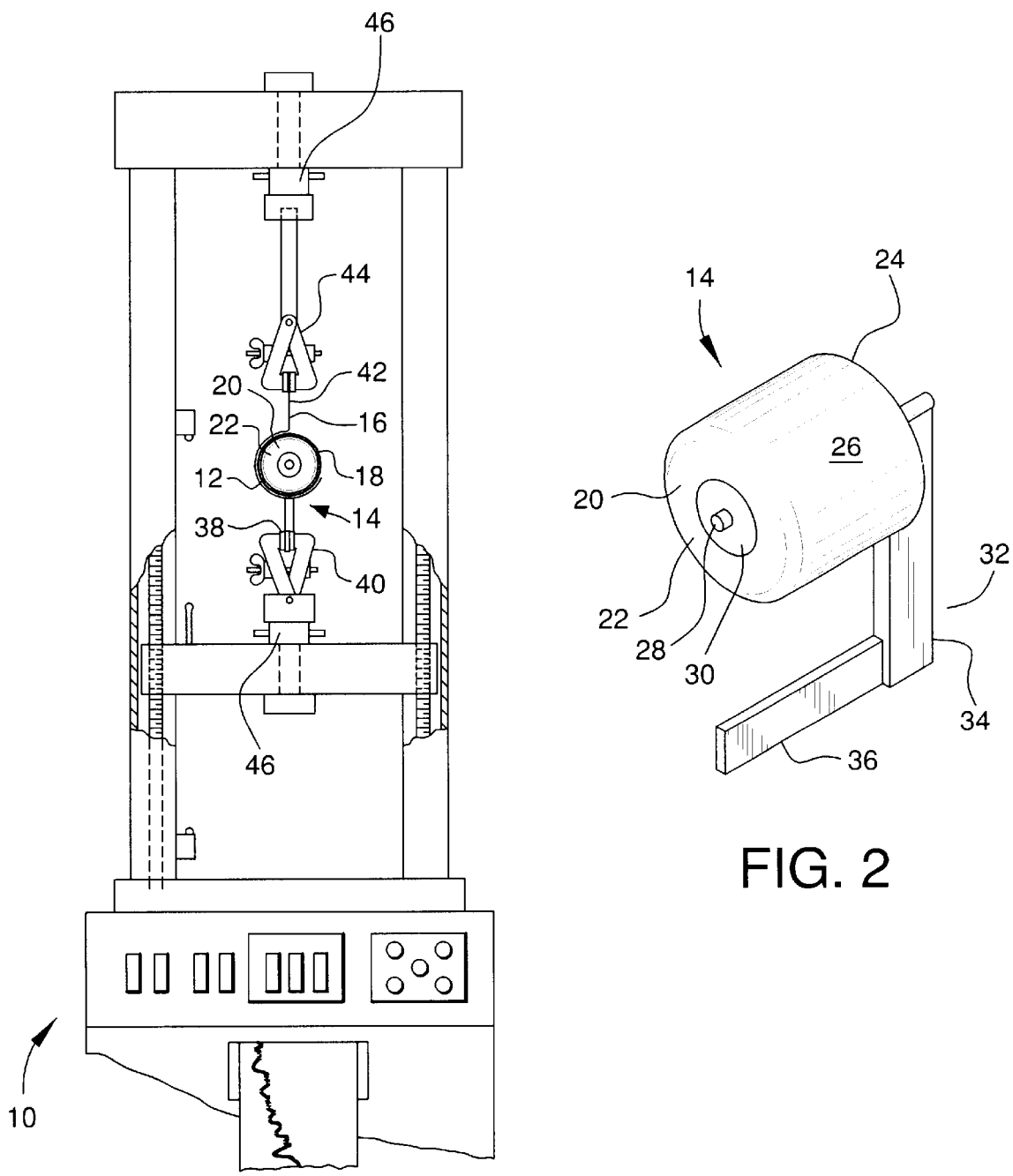

PEEL TEST MANDREL ASSEMBLY AND METHOD

Field of the Invention

The present invention generally related to a device and method for testing physical properties of materials. In particular, the present invention relates to devices and methods for testing the peel strength between adjacent layers of a laminate.

BACKGROUND OF THE INVENTION

In the manufacturing of many products it is desirable to test the peel strength between adjacent layers of a laminate. In particular, manufacturers of refrigerated dough containers test the peel strength between layers of their multilayer containers. This type of container generally has a cylindrical, tubular sidewall that includes an inner foil layer, an intermediate cardboard layer and an outer foil-paper composite layer. The inner foil layer provides an airtight envelope and a contact surface for the dough. The cardboard layer, which is relatively stiff, generally gives the container its cylindrical shape. The composite layer provides the container with an opening means and typically serves as a product label as well.

In the above-mentioned dough containers, the inner foil layer is adhesively bonded to the inner surface of the cardboard layer. The helical joint between adjacent edges of the inner foil strip lies substantially along the helical joint in the cardboard and is hermetically sealed. The composite layer comprises an inner paper layer bonded to an outer foil layer. The paper layer is adhesively bonded to the outer surface of the cardboard layer. The joint formed between adjacent edges of the composite strip is offset from the joints in the cardboard and foil layers.

When the container is filled with dough and sealed, it is under internal pressure. The offset between the joint in the composite layer and the joints in the cardboard and inner foil layers gives the container strength to resist the internal pressure. The adjacent edges of the cardboard strips are not fastened together and the joint in the inner foil layer is too weak to contain the internal pressure. Without the composite layer, the container would burst open along the joints in the those layers. To open the container, a user peels a strip of the outer composite layer from the container along the underlying joints so that they split apart and allow access to the dough within the container.

The bursting strength of the container is partly dependent on the peel strength between the composite and cardboard layers. Also, the thickness of the composite layer is dependent on the peel strength. If the bond between the layers is too strong, the composite will fail in tension before it can be peeled from the cardboard. Therefore, in order to determine a proper structural design, container manufacturers desire to test the peel strength between the layers. Manufacturers also want to test the peel strength in order to determine the force that a consumer must exert to open the container. If the containers are difficult to open, consumer will avoid buying a product sold in the container. In addition, manufacturers test the peel strength in order to determine production quality and to determine the optimal materials for constructing the containers.

Conventional peel testing of refrigerated dough containers includes clamping a sample, typically a one-inch length of a container, directly into a lower clamp on a conventional constant-rate-of-extension testing machine. A starting portion of the composite layer is peeled from the cardboard layer near the bottom of the sample and clamped into an upper clamp on the testing machine. The testing machine is started, and the composite layer is peeled from the cardboard layer while the peeling force is measured and recorded.

One shortcoming of this procedure is that the peeling force results are not linear because the peeling angle between the outer layer and the inner layer changes during the test. This is because the sample is held fixed in relation to the lower clamp, and the composite layer is peeled from the bottom of the sample to its top. Since the outer layer is pulled from above, the peeling angle, which is defined as the angle formed between the direction of pull at the point where the peeled portion joins the unpeeled portion of the composite layer and the tangent to the outer surface of the cardboard layer at that point, varies from 0° to 90° during the test. In addition, until the location of the peeling point moves above a horizontal plane through the diameter of the sample, the peeled portion slides against the unpeeled portion of the composite layer, further distorting the test results. A second shortcoming is that the sample deforms as the composite layer is being peeled. The sidewall of the unpresurized sample is relatively thin and flexible and deflect from its cylindrical shape while the composite layer is pulled from bottom to top. This deflection causes additional non-linearity in the measurements.

Testing devices for testing the peel strength between layers of a cylindrical, tubular laminate which maintain a constant peeling angle are known. However, these devices are generally either custom testing machines which are costly to manufacture or devices that are not usable with tubular cardboard containers having low axial compressive strengths and/or are lightweight. Also, the custom machines are not readily adaptable to tubular laminates of different sizes and shapes.

SUMMARY OF THE INVENTION

The present invention includes an assembly for retaining a tubular laminate while an outer layer of the laminate is pulled from an inner layer of the laminate. The assembly includes a mandrel which has a proximal end, a distal end, a longitudinal axis and a retaining surface. The retaining surface is located between the proximal end and the distal end and is substantially concentric with the longitudinal axis. The retaining surface has an outer periphery shaped and sized to frictionally engage at least a portion of the inner surface of the laminate. The assembly also includes a mounting bracket for mounting the mandrel to a mount. The mounting bracket has a radial leg which has a proximal end located substantially along the longitudinal axis adjacent the distal end of the mandrel. The radial leg extends radially from the longitudinal axis and terminates at a distal end. The mounting bracket also has means for attaching the distal end of the radial leg to the mount. The assembly further includes means for rotatably mounting the mandrel to the proximal end of the radial leg of the mounting bracket.

BRIEF DESCRIPTION OF THE DRAWINGS

For the purposes of illustrating the invention, the drawings show a form of the invention which is presently preferred. However, it should be understood that this invention is not limited to the precise arrangements and instrumentalities shown in the drawings.

FIG. 1 is an elevational view showing a mandrel assembly of the present invention mounted in a conventional rate-of-extension testing machine along with a cylindrical laminate;

FIG. 2 is a perspective view of the mandrel assembly of the present invention.

DETAILED DESCRIPTION OF THE DRAWINGS

Figure 3:
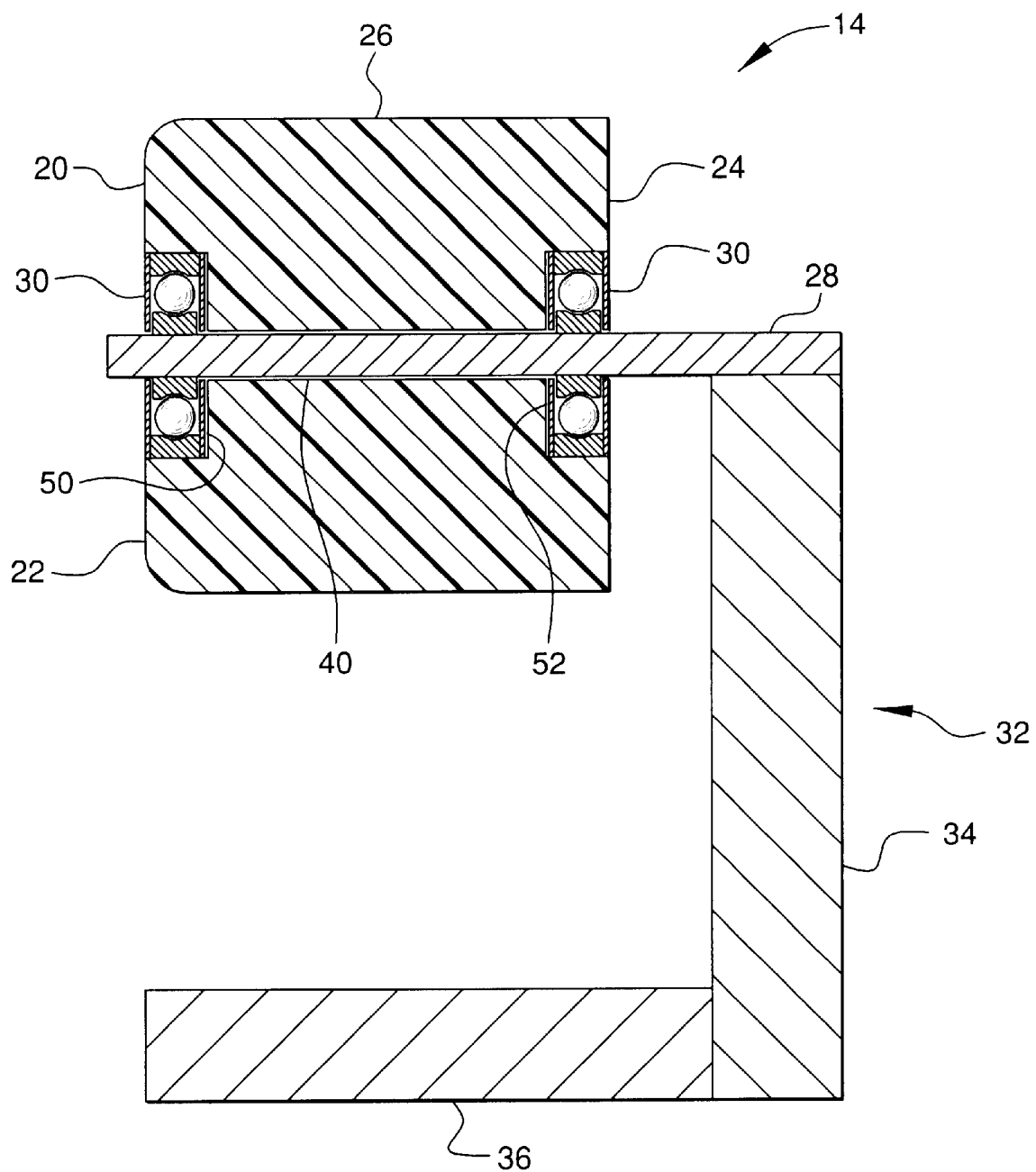
FIG. 3 is an enlarged cross-sectional view of the mandrel assembly shown in FIG. 2.

Referring to the drawings wherein like numerals indicate like elements, FIG. 1 illustrates a conventional constant-rate-of-extension testing machine, which is designated generally by the numeral 10. In accordance with the present invention, the testing machine 10 is used to test the peel strength between adjacent layers of a sample 12 of a tubular laminate. To facilitate the testing, a mandrel assembly 14 is provided to hold the sample 12 by friction fit while an outer layer 16 of the sample 12 is peeled substantially radially from an inner layer 18.

Referring to FIG. 2, the mandrel assembly 14 includes a mandrel 20 which has a proximal end 22, a distal end 24 and a retaining surface 26 located therebetween. The mandrel 20 is preferably made of plastic, such as a thermoplastic polyester based polyethylene terephthalate. Other materials such as metal, wood, ceramics or the like, however, may be used. The mandrel 20 shown is cylindrical for receiving a cylindrical sample. The preferred outside diameter of the mandrel 14 generally corresponds to the inside diameter of the containers to be tested. Also, mandrels having shapes other than cylindrical may be used for samples which are not cylindrical.

In addition, mandrels having shapes dissimilar from the shape of the sample may be used as long as the friction developed between a sample and a mandrel is sufficient for the test. For example, a cylindrical, tubular sample may be mounted to mandrel having the shape of triangle, rectangle or other polygon wherein the edges of those shapes are rounded to conform to and engage the inner surface of the sample. A tubular sample may also be mounted on a mandrel comprising two or more radial arms, the outer ends of which frictionally engage the inner surface of the sample.

It is preferred that the length of a sample be less than the length of the retaining surface 26. However, a sample may be longer. As long as a sample is sufficiently strong enough to cantilever over the proximal end 22 of the mandrel 20 and as long as sufficient friction is developed between the retaining surface 26 and the sample, any length sample may be used. The outer edge of the proximal end 22 is rounded to facilitate mounting a sample onto the mandrel 20.

The mandrel 20 is rotatably mounted on an axle 28 by a pair of rotational bearings 30, one located at the proximal end 22 and the distal end 24. The axle 28, which is preferably 5/16 inch in diameter and 3 inches long, is fixedly attached to an L-shaped mounting bracket 32 which allows the mandrel assembly 14 to be mounted to the testing machine 10. The mounting bracket 32 has a radial leg 34 and a clamping leg 36, which are preferably flat metal bars ½ inch wide by 3/16 inch thick. Preferably, the length of the radial leg 34 varies with the diameter of the mandrel 14, which on the present embodiment is approximately 3 inches long. Other shapes and materials, however, may be used. For example, the legs 32, 34 may be round or polygon shaped bars or tubes or the like and may be made of plastic, fiberglass or the like. One end of the radial leg 34 is fixedly attached to the axle 28. Although it is preferred that the radial leg 34 be welded to the axle, other means such as clamping, bonding, mechanical fastening or the like may be used.

The clamping leg 38 is substantially parallel to the axle 28 and is fixedly attached to the radial leg 36, for example, by welding. The clamping leg 36 is preferably 2½ inches long and is configured to be clamped between the jaws 38 of a clamp-type assembly mount 40 attached to the testing machine 10. Although the mounting bracket 32 is shown having the clamping leg 38 as the means of mounting the mandrel assembly to a testing machine, other mounting means may be used. For example, the mounting means may be configured to attach to a clevis mount, a threaded mount, a bayonet mount or the like. Regardless of the type of mount, it is preferred that the mandrel assembly 14 be held in fixed relation to the mount such that the axle 28 is substantially perpendicular to the direction of pull and the outer layer 16 is pulled substantially radially from the inner layer 18. Alternatively, the mandrel assembly 14 may be pivotally mounted such that the two foregoing orientations are achieved when tension is applied to the peeled portion of the outer layer 16.

To conduct a peel test, the sample 12, for example a one-inch length of a cylindrical refrigerated dough container, is sleevedly mounted to the mandrel 20 by sliding it over the proximal end 22. The inner surface of the tubular sample 12 frictionally engages the retaining surface 26 on the outer periphery of the mandrel 20. The diameter of the mandrel 20 is selected to snugly fit the sample 12 to prevent it from slipping relative to the mandrel 20 during testing. However, the fit is not so snug that mounting and removing the sample 12 is burdensome. After mounting the sample 12 onto the mandrel 20, the mandrel assembly 14 is clamped into the assembly mount 40 on the testing machine 10.

A starting end 42 of the outer layer 16 is pulled from the inner layer 18 and clamped into a sample clamp 44. Alternatively, a fixture (not shown) may be attached to the starting end 42 which allows the starting end 42 to be mounted to the testing machine 10 by means other than a clamp, such as a clevis mount, threaded mount or the like. The fixture may be bonded, mechanically fastened or the like to the starting end 42. In a further alternative, the fixture or a portion thereof may be bonded directly to the outer layer 16 without peeling a portion to create a starting end. In this case, the initial break-away strength of the outer layer may be tested in addition to the peel strength. The fixture for this type of test may be flexible, hinged or the like so that the direction of pull remains substantially radial to the sample 12.

After the starting end 42 of the outer layer 16 has been clamped into the sample clamp 44, the testing machine 10 is started. The testing machine 10 moves the assembly mount 40 and the mandrel assembly 14 downward and away from the fixed sample clamp 44 at a constant rate of speed. While the outer layer 16 is peeled from the inner layer 18, the pulling force required to peel the outer layer 16 from the inner layer 18 is measured by one or more load cells 46, and that force is recorded by the testing machine 10. During the peel test, the mandrel 20 rotates relatively freely, causing the outer layer 16 to be peeled substantially radially from the inner layer 18, resulting in a peeling angle of substantially 90°. The peeling angle is defined as the angle formed between the direction of pull at the point where the peeled portion is joined to the unpeeled portion of the outer layer ans a tangent to the outer surface of the inner layer at that point. The substantially constant peeling angle eliminates the need to adjust test results for a varying peeling angle as is necessary when utilizing known peel testing procedures.

Referring now to FIG. 3, there is shown an enlarged cross-sectional view of the mandrel assembly 14 shown in FIG. 2. FIG. 3 illustrates that the mandrel 20 is rotatably mounted on the axle 28 by a pair of rotational bearings 30.

The axle 28 projects through a passageway 48 within the mandrel 20. The axle 28 and the passageway 48 are concentric with the retaining surface 26. One bearing 30 is located in a proximal recess 48 within the mandrel 20, and the other is located in a distal recess 50. Each of the bearings 30 is press fit into the corresponding recess 48, 50 and press fit onto the axle 28. Preferably, the bearing 30 meets the ABEC-3 standard of the Annular Bearing Engineers Committee. Although the bearings 30 are shown as being press fit into the recesses 50, 52, the being may be bonded, mechanically fastened or the like into the recesses 50, 52. Similarly, instead of the bearings 30 being press fit to the axle 28, they may be retained by welding, bonding, using a collar and cotter pin, using a collar and set screw, using lock washers or the like. In addition, the bearing 30 may be replaced by one or more bearings of a different type, such as one in which the an inner periphery of the mandrel 20 is an outer race and the surface of the axle is an inner race for a plurality of roller bearings.

FIG. 3 also shows the rounded outer edge of the proximal end 22 of the mandrel 20 which aids a user when mounting a test sample onto the retaining surface 26. The rounded edges guides a sample onto the mounting surface 26 and prevents the leading edge of the sample from being damaged. The outside diameter of the mandrel 20 must be slightly larger than the inside diameter of a sample in order to create a tight fit that prevents slippage between a sample and the retaining surface 26. Without a rounded outer edge on the proximal end 22, it would be very difficult to mount a sample having, for example, a cardboard inner layer without damaging the leading edge of that layer. Although a rounded edge is shown, the edge may be beveled or otherwise tapered.

Although the invention has been described and illustrated with respect to the exemplary embodiment thereof, it should be understood by those skilled in the art that the foregoing and various other changes, omissions and additions may be made therein and thereto, without parting from the spirit and scope of the present invention.

We claims:

1. An assembly for retaining a tubular laminate while an outer layer of the laminate is peeled from an adjacent inner layer of the laminate, the assembly comprising:

a mandrel having a proximal end, a distal end, a longitudinal axis, and a retaining surface which is located between the proximal end and the distal end and is substantially concentric with the longitudinal axis, the retaining surface having an outer periphery shaped and sized to frictionally engage at least a portion of the inner surface of the laminate, the proximal end having a tapered edge which tapers inwardly toward the longitudinal axis from the retaining surface to the proximal end;

a mounting bracket for mounting the mandrel to a mount; and a means for rotatably mounting the mandrel to the mounting bracket adjacent the distal end of the mandrel.

2. The assembly of claim 1 wherein the mandrel is cylindrical.

3. The assembly of claim 2 wherein the mandrel is made of plastic.

4. The assembly of claim 1 wherein the mounting bracket is L-shaped and is attached to the mandrel such that the mandrel and the bracket form a C-shape.

5. The assembly of claim 1 wherein the means for rotatably mounting the mandrel to the mounting bracket includes an axle fixedly attached to the mounting bracket and at least one rotational bearing which engages the mandrel and the axle such that the mandrel is rotatable on the axle.

6. The assembly of claim 5 wherein a proximal bearing is located in a proximal recess in the proximal end of the mandrel and a distal bearing is located in a distal recess in the distal end of the mandrel.

* * * * *